United States Patent

Fairhurst

Patent Number: 5,929,072
Date of Patent: *Jul. 27, 1999

[54] 1H-2,1,3-BENZOTHIADIAZINE-2,2-DIOXIDE COMPOUNDS OR DERIVATIVES THEREOF

[75] Inventor: John Fairhurst, Winchester, United Kingdom

[73] Assignee: Eli Lilly and Company Limited, Basingstoke, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/137,788

[22] Filed: Aug. 21, 1998

[51] Int. Cl.⁶ .................. A61K 31/54; C07D 279/00; C07D 285/16

[52] U.S. Cl. .................. 514/222.8; 544/6; 544/11

[58] Field of Search ............... 544/6, 11; 514/222.8

[56] References Cited

U.S. PATENT DOCUMENTS

| | | | |
|---|---|---|---|
| 4,113,939 | 9/1978 | Fischer et al. | 544/11 |
| 4,189,572 | 2/1980 | Pews | 544/11 |
| 5,130,313 | 7/1992 | Comte et al. | 514/253 |
| 5,670,511 | 9/1997 | Marz et al. | 514/290 |

FOREIGN PATENT DOCUMENTS 0 854 146 A1  7/1998  European Pat. Off. .

OTHER PUBLICATIONS

Knollmuller, M., *Monatshefte Fur Chemie,* 102 (5): 1583–92 (1971).

Primary Examiner—Mukund J. Shah
Assistant Examiner—Tamthom T. Ngo
Attorney, Agent, or Firm—Suzanne M. Harvey; Robert D. Titus

[57] ABSTRACT

A pharmaceutical compound having the formula:

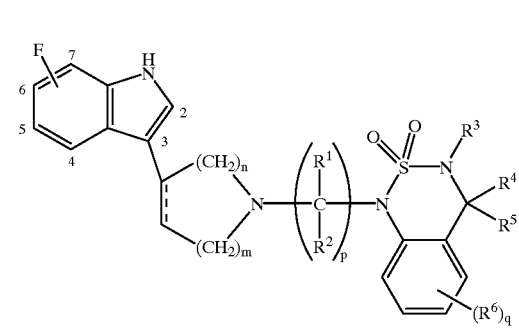

(I)

in which n is 1 or 2, m is 1 or 2, p is 1 to 6, q is 0 or 1 to 3, $R^1$ and $R^2$ are each hydrogen or $C_{1-4}$ alkyl, $R^3$, $R^4$ and $R^5$ are each hydrogen, $C_{1-4}$ alkyl, optionally substituted phenyl or optionally substituted phenyl-$C_{1-4}$ alkyl, or $R^3$ and $R^4$ together form an alkylene link of formula —$(CH_2)_3$— or —$(CH_2)_4$—, or $R^4$ and $R^5$ together with the carbon atom to which they are attached form a $C_{3-6}$ cycloalkyl group, $R^6$ is $C_{1-4}$ alkyl, $C_{1-4}$ alkoxy, carboxy, hydroxy, cyano, halo, trifluoromethyl, nitro or amino, the dotted line represents an optional double bond, and the fluorine atom is attached at the 6 or 7-position;

and salts and esters thereof.

8 Claims, No Drawings

1H-2,1,3-BENZOTHIADIAZINE-2,2-DIOXIDE COMPOUNDS OR DERIVATIVES THEREOF

This application claims the benefit of United Kingdom Application Nos. 9717832.1 filed Aug. 22, 1997 and 9815388.5 filed Jul. 15, 1998.

This invention relates to novel compounds with pharmaceutical properties.

It is well known that compounds active at serotonin receptors have potential in the treatment of disorders of the central nervous system and, for example, certain halo-substituted indole compounds having serotonin antagonist properties are disclosed in EP-A 0433149.

The compounds of the invention are of the following formula:

(I)

in which n is 1 or 2, m is 1 or 2,
p is 1 to 6, q is 0 or 1 to 3,
$R^1$ and $R^2$ are each hydrogen or $C_{1-4}$ alkyl,
$R^3$, $R^4$ and $R^5$ are each hydrogen, $C_{1-4}$ alkyl, optionally substituted phenyl or optionally substituted phenyl-$C_{1-4}$ alkyl, or $R^3$ and $R^4$ together form an alkylene link of formula —$(CH_2)_3$— or —$(CH_2)_4$—, or $R^4$ and $R^5$ together with the carbon atom to which they are attached form a $C_{3-6}$ cycloalkyl group,
$R^6$ is $C_{1-4}$ alkyl, $C_{1-4}$ alkoxy, carboxy, hydroxy, cyano, halo, trifluoromethyl, nitro or amino,
the dotted line represents an optional double bond, and
the fluorine atom is attached at the 6 or 7-position;
and salts and esters thereof.

The compounds of the invention and their pharmaceutically acceptable salts and esters are indicated for use in the treatment of disorders of the central nervous system.

A $C_{1-4}$ alkyl group can be methyl, ethyl or propyl and can be branched or unbranched and includes isopropyl and tert. butyl. A $C_{1-4}$ alkoxy group is one such $C_{1-4}$ alkyl group attached through oxygen to the ring. An optionally substituted phenyl-$C_{1-4}$ alkyl group is an optionally substituted phenyl attached through one such $C_{1-4}$ alkyl group, and is preferably optionally substituted phenyl-$(CH_2)_x$— where x is 1 or 2, and most preferably optionally substituted benzyl. A halo substituent is preferably fluoro, chloro or bromo.

An optionally substituted phenyl group is optionally substituted with one or more, preferably one to three, substitutents selected from, for example $C_{1-4}$ alkyl, $C_{1-4}$ alkoxy, carboxy, hydroxy, cyano, halo, trifluoromethyl, nitro and amino.

Preferably $R^3$ and $R^4$ are each hydrogen, $C_4$ alkyl, optionally substituted phenyl or optionally substituted phenyl-$C_{1-4}$ alkyl, and $R^5$ is hydrogen.

It will be appreciated that when p is more than one, the recurring unit is not necessarily the same, and when q is 2 or 3 the values of $R^6$ need not be the same.

A preferred group of compounds is one of formula (I) above, in which the dotted line represents a double bond, n is 2 and m is 1, $R^1$ and $R^2$ are both hydrogen, p is 2, $R^3$ is $C_{1-4}$ alkyl, $R^4$ and $R^5$ are hydrogen and q is 0 or 1.

Preferred compounds are those which exhibit one or more of the following features:
(i) the fluorine substituent is in the 6-position
(ii) the dotted line represents a double bond
(iii) n is 2 and m is 1
(iv) $R^1$ and $R^2$ are both hydrogen
(v) p is 2
(vi) $R^3$ is $C_{1-4}$ alkyl, especially isopropyl
(vii) $R^4$ and $R^5$ are hydrogen
(viii) q is 0 or 1, and preferably 0
(ix) $R^6$ is $C_{1-4}$ alkoxy, hydroxy, halo or amino, and especially amino(—$NH_2$).

A particularly preferred group of compounds is of the formula:

(II)

in which $R^3$ is $C_{1-4}$ alkyl and especially isopropyl, or a pharmaceutically acceptable salt thereof.

As indicated above, it is, of course, possible to prepare salts of the compound of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

It will be appreciated that when a phenyl substituent is acidic such as, for example, a carboxy group, the opportunity exists for esters. These can be aliphatic or aromatic, being preferably alkyl esters derived from $C_{1-4}$ alkanols, especially methyl and ethyl esters. An example of an ester substituent is —COOR' where R' is $C_{1-4}$ alkyl.

Some of the compounds of the invention contain one or more asymmetric carbon atoms which gives rise to isomers. These compounds are normally prepared as racemic mixtures and can conveniently be used as such, but individual isomers can be isolated by conventional techniques, if so desired. Such racemic mixtures and individual optical isomers form part of the present invention. It is preferred to use an enantiomerically pure form.

The invention also includes a process for producing a compound of formula (I) above, which comprises reacting a compound of the formula:

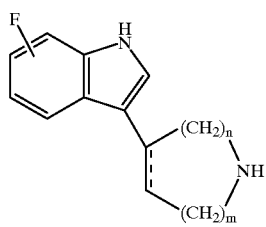
(III)

with a compound of the formula:

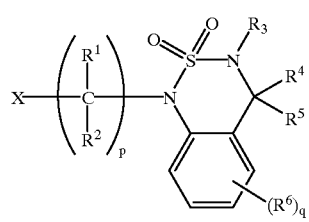
(IV)

where the substituents have the values given above, and X is a leaving group such as, for example, a halo atom, or a mesylate or tosylate. The coupling can also be effected by reacting the compound of formula (III) with an aldehyde equivalent of the compound of formula (IV). Such aldehydes can be prepared from the appropriate terminal alkene by oxidation employing, for example, ozone or osmium tetroxide, followed by reductive amination using, for example, sodium cyanoborohydride, borane in pyridine or triacetoxy borohydride, and the compound of formula (III).

The reaction is preferably carried out in a polar solvent such as, for example, acetonitrile or water, at a temperature of from 50° C. to 150° C., and in the presence of sodium iodide and a base such as, for example, sodium carbonate.

The intermediate compounds of formula (III) are known in the art, whereas compounds of formula (IV) are novel. The latter can be prepared by reacting the appropriate alkane derivative of formula:

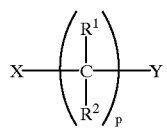
(V)

where X is a leaving group, and Y is halo, preferably bromo, with a compound of formula:

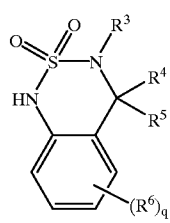
(VI)

Preferred alkane reactants are dihalo-alkanes, for instance bromo chloroethane, and the reaction is preferably carried out in an organic solvent such as, for example, dimethyl formamide, with a strong base such as sodium hydride, at a temperature of from 0° C. to 100° C., for instance room temperature.

Some of the intermediate compounds of formula (VI) are known in the literature, and they can readily be prepared by a variety of routes, the principal route being a trioxan catalysed reaction between the appropriate sulphamoyl compound prepared from an aniline and sulphamoyl chloride, and an alkyl sulphonic acid as, for example:

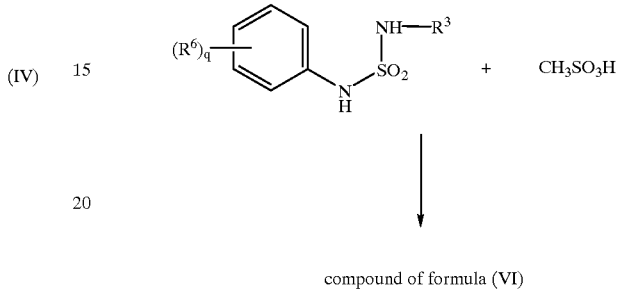

compound of formula (VI)

Other aldehydes or ketones can be used in the reaction instead of trioxan to produce compounds in which $R^4$ is other than hydrogen.

An alternative synthesis of compounds of formula (VI) is by reductive animation and cyclisation, starting from a nitro aldehyde as, for example:

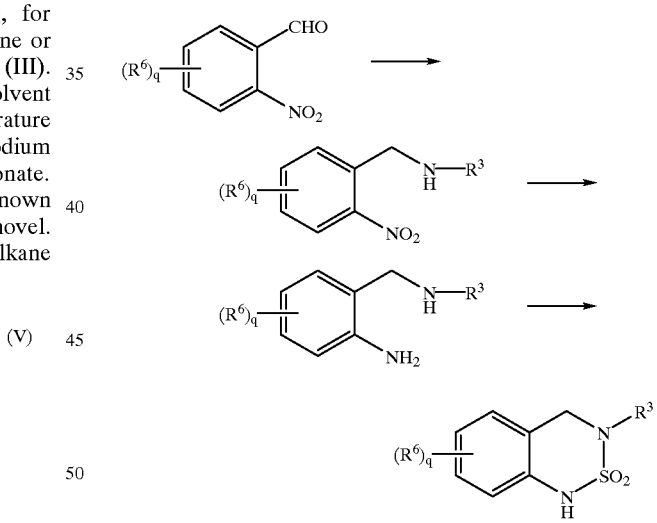

The last step can be carried out by reaction of $H_2NSO_2NH_2$ in pyridine or diglyme. Instead of starting with the nitro aldehyde, it is possible to substitute a ketone, such as ortho-nitro acetophenone, which allows the synthesis of compounds of formula (I) in which $R^4$ is other than hydrogen.

As indicated above, the compounds of formula (I) can be produced by reacting a compound of formula (III) with an appropriate aldehyde intermediate. The latter can be prepared by oxidation of the corresponding alkene prepared, for example, in the following manner (this route is especially useful for preparing compounds where $R^3$, $R^4$ or $R^5$ is other than hydrogen).

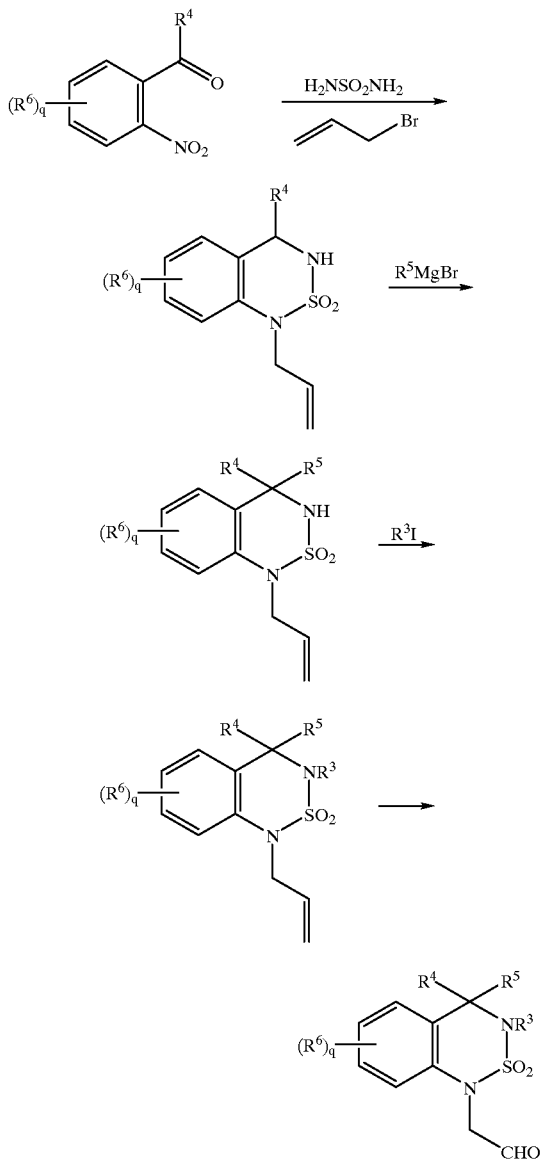

As mentioned above, the compounds of the invention and their pharmaceutically acceptable salts have useful central nervous system activity. The compounds are active at the serotonin, 5-HT2A, receptor. Their binding activity has been demonstrated in a test described by Nelson, D. L. et al, J. Pharmacol. Exp. Ther., 265, 1272–1279, in which the affinity of the compound for the human 2A receptor is measured by its ability to displace the ligand [$^3$H] ketanserine. In this test, the compounds of the invention in the following Examples had a Ki of less than 15 nM. The compounds of the invention are also active serotonin reuptake inhibitors as measured by their displacement of [$^3$H] paroxetine at the reuptake site, Neuropharmacology Vol. 32 No. 8, 1993, pages 737–743.

Because of their selective affinity for 5-HT receptors, the compounds of the present invention are indicated for use in treating a variety of conditions such as depression, obesity, bulimia, alcoholism, pain, hypertension, ageing, memory loss, sexual dysfunction, anxiety, schizophrenia, gastrointestinal disorders, headache, cardiovascular disorders, smoking cessation, drug addiction, emesis, Alzheimer's and sleep disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or ester thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.5 to 100 mg, more usually 1 to 100 mg, of the active ingredient.

The following Preparations and Examples illustrate routes to the synthesis of the compounds of the invention.

PREPARATION 1

6-Fluoroindole

1-Dimethylamino-2-(4-fluoro-2-nitro)phenylethene

A mixture of 4-fluoro-2-nitrotoluene (50 g, 0.32 mol), dimethylformamide dimethylacetal (76.77 g) and dimethylformamide (910 ml) were heated under reflux under nitrogen with stirring for 7 hours, cooled, allowed to stand for 16 hours, poured into ice-water (2000 ml), stirred for 15 minutes and the resultant precipitate isolated by filtration, washed with water (500 ml), dried to give a red solid.

6-Fluoroindole

A 40 litre Cook hydrogenator was charged under a nitrogen atmosphere with 10% palladium on charcoal (9 g) suspended in toluene (400 ml). To this suspension was added 1-dimethylamino-2-(4-fluoro-2-nitro)phenylethene (137.2 g, 0.653 mol) in toluene (1400 ml) and the mixture hydrogenated at 80 psi for 3.5 hours. The suspension was then filtered through a celite pad, which was washed through with toluene (2×200 ml) and the filtrate and washings evaporated under reduced pressure to give a brown oil which crystallised on standing to a yellow brown solid 93.65 g. This solid was dissolved in ethyl acetate-hexane (7:3) and filtered through a pad of flash silica. The required fractions were collected and evaporated under reduced pressure to give a pale brown solid.

PREPARATION 2

7-Fluoroindole

2 Fluoronitrobenzene (20.0 g, 0.142 mol) was dissolved in dry tetrahydrofuran (400 ml) and cooled to −50° C. Vinylmagnesium chloride (288 ml, 15% wt/vol) was added at −45° C. and stirred at this temperature for one hour. Poured onto saturated ammonium chloride (600 ml). Separated and aqueous extracted with diethyl ether (2×200 ml). Dried (MgSO4), filtered and concentrated in vacuo to yield a dark oil which was purified by column chromatography on silica using toluene as mobile phase. Fractions concentrated to yield a crystalline solid.

7-Fluoroindole(alternative preparation)

To a stirred solution of boron trichloride in dichloromethane (1.0 M, 3.650 l, 3.65 mol) at −10° C. under nitrogen was added 2-fluoroaniline (387 g, 3.48 mol) and the temperature rose to 18° C. The mixture was stirred for 45 minutes before chloroacetonitrile (300 g, 3.97 mol) followed by aluminium chloride (500 g, 3.75 mol). 1,2-Dichloroethane (5.7l) was added the mixture heated and the dichloromethane distilled from the reaction vessel. The dichloroethane solution was then heated at 78–80° C. for 18 hours. The reaction mixture was then cooled to 2° C. and hydrochloric acid (2.5 M, 450 ml) was added slowly with a resultant exotherm. More hydrochloric acid (2.5 M, 5.550 l) was added and then the mixture was warmed to reflux for 10 minutes then cooled. The dichloroethane layer was separated and the aqueous layer extracted with dichloromethane (1 l) combined with the dichloroethane, washed with brine (2 l), dried (MgSO4), filtered and the solvent evaporated in vacuo to give a solid 321.7 g. This solid was dissolved in a mixture of dioxan (10 l) and water (1 l) and treated under nitrogen with sodium borohydride (73.0 g, 1.93 mol) then heated under reflux for 1 hour. More sodium borohydride (12 g) was added and the mixture heated for a further 3 hours, cooled to 45° C. and the solvent removed in vacuo. The residue was partitioned between dichloromethane (2000 ml) and water (2000 ml). The organic layer was separated, dried (MgSO4), filtered and evaporated in vacuo to give an oil which was further purified by filtering through silica.

PREPARATION 3

4-(6-Fluoroindol-3-yl)-1,2,5,6-tetrahydropyridine

Powdered potassium hydroxide (144.4 g) was added carefully to a mechanically stirred mixture of 6-fluoroindole (49.23 g, 0.364 mol) and 4-piperidone monohydrate (111.93 g, 0.728 mol) in methanol (1500 ml). The mixture was then heated under reflux under nitrogen for 18 hours and then more potassium hydroxide (40 g) was added and the reaction mixture heated under reflux for a further 4 hours. The reaction mixture was allowed to cool to room temperature and poured onto ice-water (3000 ml) and stirred for 1 hour and the precipitated solid isolated by filtration and dried at 50° C. in vacuo to give a solid.

PREPARATION 4

4-(6-Fluoroindol-3-yl)piperidine

A mixture of platinum oxide (1.0 g) in ethanol (37.5 ml) and glacial acetic acid (12.5 ml) was treated under nitrogen with 4-(6-fluoroindol-3-yl)-1,2,5,6-tetrahydropyridine (20 g, 92.6 mmol) in ethanol (187.5 ml) and glacial acetic acid (62.5 ml). The nitrogen was evacuated and hydrogen was admitted. The reaction mixture was then hydrogenated at 60 psi until the reaction was complete by tlc. The catalyst was removed by filtration and the solvent evaporated in vacuo to give a yellow solid which was dried at 60° C. in vacuo.

Similarly prepared was 4-(7-fluoroindol-3-yl)-piperidine from 4-(7-fluoroindol-3-yl)-1,2,5,6-tetrahydropyridine.

PREPARATION 5

3,4-Dihydro-3-(1-methylethyl)-1H-2,1,3-benzothiadiazine-2,2-dioxide

1) A 250 ml 3-necked round bottom flask equipped with a magnetic stirrer bar, pressure equalising dropping funnel, thermometer and nitrogen gas bleed was charged with nitromethane (75 ml) and fuming sulfuric acid (30 g, i.e. oleum 12–17%). The mixture was cooled to 0° C. using an external cardice (solid CO2)/acetone bath. Then isopropyl isocyanate (25 g, 0.294 mol) was added dropwise to the mixture, stirred under nitrogen, keeping the temperature below 30° C. during the addition. The stirred suspension was then heated under reflux for 30 minutes, then allowed to cool to room temperature and stirred overnight.

Diethyl ether (100 ml) was added to the mixture, which was then filtered. The filter pad was washed with more ether (3×100 ml) and then dried in an air stream at room temperature to give a pale yellow crystalline solid, isopropyl sulfamic acid.

2) A 500 ml 3-necked round bottom flask equipped with a water condenser, thermometer and magnetic stirrer bar was charged with isopropylsulfamic acid (34.8 g, 0.25 mol), phosphorus pentachloride (52.06 g, 0.25 mol) and toluene (400 ml). The mixture was warmed under reflux for 1 hour, then cooled back down to room temperature. The solvent was removed in vacuo to give a pale brown oil which was then purified by distillation under reduced pressure (approximately 15 mm Hg and 110° C.) to give a clear, colourless liquid, isopropyl sulfamoyl chloride.

3) A 100 ml 3-necked round bottom flask equipped with a magnetic stirrer bar, thermometer and pressure equalising dropping funnel was charged with aniline (36.7 g, 0.39 mol, 2.2 mol equivalent) and toluene (500 ml). The solution was cooled to 5° C. and then isopropylsulfamoyl chloride (28.2 g, 0.179 mol) was added dropwise. The mixture was allowed to warm up to room temperature and stirred overnight. The solvent was removed in vacuo and the residue suspended in water (500 ml) and extracted with ethyl acetate (2×250 ml). The bulked extracts were washed with water and then dried over magnesium sulfate. Filtration was followed by evaporation to dryness in vacuo to give a cream coloured solid as product, N-phenyl-N'-(1-methylethyl)sulfamide.

4) A 500 ml 3-necked round bottom flask equipped with a thermometer, magnetic stirrer bar and pressure equalising dropping funnel was charged with N-phenyl-N'-(1-methylethyl)sulfamide (18.64 g, 86.8 mmol), dichloromethane (166 ml) and methane sulfonic acid (105 ml). The stirred mixture was cooled to 5° C. using an external ice-bath. Then a solution of trioxane (2.58 g, 28.7 mmol) in dichloromethane (83 ml) was added rapidly (exotherm to 17° C.) and the reaction mixture was cooled back to 5° C. The reaction mixture was poured onto ice/water and the organic layer separated. This organic layer was washed with water (3×100 ml) and then dried over magnesium sulfate. Filtration was followed by evaporation to dryness in vacuo to give a brown oil as product, 3,4-dihydro-3-(1-methylethyl)-1H-2,1,3-benzothiadiazine-2,2-dioxide. (See also J.O.C. 44, 1979, pp 2032–34.)

Similarly prepared:

3,4-Dihydro-6-methoxy-3-(1-methylethyl)-1H-2,1,3-benzothiadiazine-2,2-dioxide from 4-methoxy aniline and isopropylsulfamoyl chloride.

Ethyl 3,4-dihydro-2,2-dioxo-3-(1-methylethyl)-1H-2,1,3-benzothiadiazine-6-carboxylate from ethyl 4-aminobenzoate and isopropylsulfamoyl chloride.

3,4-Dihydro-6-fluoro-3-(1-methylethyl)-1H-2,1,3-benzothiadiazine-2,2-dioxide from 4-fluoroaniline and ispropylsulfamoyl chloride.

3,4-Dihydro-3-(1-methylethyl)-6-trifluoromethyl-1H-2,1,3-benzothiadiazine-2,2-dioxide from 4-trifluoromethylaniline and isopropylsulfamoyl chloride.

3,4-Dihydro-3-methyl-1H-2,1,3-benzothiadiazine-2,2-dioxide from aniline and methanesulfamoyl chloride (prepared according to the method of Weiss G et al, Justus Liebigs Ann Chem 40 (1969)).

3,4-Dihydro-3-(1-methylethyl)-1H-2,1,3-benzothiadiazine-2,2-dioxide (alternative preparation)

To a 500 ml 3-necked round bottom flask equipped with overhead mechanical stirrer, thermometer and nitrogen bubbler was charged 2-nitrobenzaldehyde (200 g, 1.32 mol) in methanol (1300 ml), to which was added isopropylamine (78.0 g, 113 ml, 1.32 mol) in one portion with stirring under nitrogen. The reaction mixture was then stirred for 100 minutes (followed reaction by GC), then added to a 4 litre stainless steel Parr hydrogenator, containing a suspension of 5% palladium on charcoal (13.24 g, 6% cat. loading) in methanol (500 ml) and the suspension hydrogenated under hydrogen at 60 psi for 3 hours. The suspension was filtered through a pad of celite, the pad washed with methanol (500 ml) and the combined filtrate evaporated under reduced pressure to leave a yellow oil, 2-amino-N-(1-methylethyl)-benzylamine.

To a 500 ml 3-necked round bottom flask equipped with reflux condenser, thermometer, magnetic stirrer bar and nitrogen bubbler was charged 2-amino-N-(1-methylethyl)-benzylamine (148.0 g, 0.907 mol), sulfamide (87.9 g, 0.907 mol) and pyridine (975 ml) and the stirred solution heated at reflux for 5 hours under nitrogen (reaction followed by GC and HPLC). The reaction mixture allowed to cool, then pyridine removed under reduced pressure. The residue was dissolved in 5N hydrochloric acid (1000 ml) and ethyl acetate (1000 ml) and the acidic layer was extracted with further ethyl acetate (5×1000 ml). The combined organic layer was washed with 5N hydrochloric acid (250 ml), then extracted with 2N sodium hydroxide (3×1000 ml), the combined aqueous layer washed with diethyl ether (2×500 ml). Ice was then added to the aqueous layer, followed by addition of 5N hydrochloric acid with cooling and stirring of the suspension to pH 1. The oily suspension was stirred at room temperature overnight, the solid filtered and dried at room temperature under vacuum to leave an off-white solid, 3,4-dihydro-3-(1-methylethyl)-1H-2,1,3-benzothiadiazine-2,2-dioxide.

Similarly prepared were, 3,4-Dihydro-3-(but-1-yl)-1H-2,1,3-benzothiadiazine-2,2-dioxide from n-butylamine and 2-nitrobenzaldehyde.

3,4-Dihydro-3-(1-methylpropyl)-1H-2,1,3-benzothiadiazine-2,2-dioxide from (1-methylpropyl) amine and 2-nitrobenzaldehyde.

3,4-Dihydro-3-ethyl-1H-2,1,3-benzothiadiazine-2,2-dioxide from ethylamine and 2 nitrobenzaldehyde.

3,4-Dihydro-3-prop-1-yl-1H-2,1,3-benzothiadiazine-2,2-dioxide from n-propylamine and 2-nitrobenzaldehyde.

3,4-Dihydro-3-(2-methylprop-1-yl)-1H-2,1,3-benzothiadiazine-2,2-dioxide prepared from 2-nitrobenzaldehyde and 2-methylprop-1-ylamine.

3,4-Dihydro-3-(1,1-dimethylethyl)-1H-2,1,3-benzothiadiazine-2,2-dioxide prepared from 2-nitrobenzaldehyde and 1,1-dimethylethylamine.

4-Methyl-1H-2,1,3-benzothiadiazine-2,2-dioxide prepared from 2-aminoacetopheneone and sulfamide.

PREPARATION 6

1-(2-Chloroethyl)-3,4-dihydro-3-(1-methylethyl)-1H-2,1,3-benzothiadiazine-2,2-dioxide 3,4-Dihydro-3-(1-methylethyl)-1H-2,1,3-benzothiadiazine-2,2-dioxide (16.725 g, 74.1 mmol) was dissolved in DMF (400 ml) and then treated with sodium hydride (3.26 g, 60% oil dispersion, 81.5 mmol, 1.1 equivalent). The mixture was stirred at room temperature and under nitrogen for 45 minutes. 1-Bromo-2-chloroethane (7.4 ml, 12.75 g, 88.9 mmol, 1.2 equivalent) was added in one portion to the stirred mixture, and stirred overnight at room temperature. The solvent was removed in vacuo and the residue suspended in water and extracted into ethyl acetate (3×150 ml). The bulk extracts were washed with water (3×100 ml) and brine, then dried over magnesium sulfate. Filtration was followed by evaporation to dryness in vacuo and the residue (approximately 22 g) chromatographed on silica using dichloromethane as eluent.

This gave a white solid [1-(2-chloroethyl)-3,4-dihydro-3-(1-methylethyl)-1H-2,1,3-benzothiadiazine-2,2-dioxide].

Similarly prepared were:

3,4-Dihydro-1-(3-chloroprop-1-yl)-3-(1-methylethyl)-1H-2,1,3-benzothiadiazine-2,2-dioxide using 1 bromo-3-chloropropane.

3,4-Dihydro-1-(4-chlorobut-1-yl)-3-(1-methylethyl)-1H-2,1,3-benzothiadiazine-2,2-dioxide using 1 bromo-4-chlorobutane.

EXAMPLE 1

3,4-Dihydro-1-{2-[4-(6-fluoroindol-3-yl)-1,2,5,6-tetrahydro-1-pyridyl]-1-ethyl}-3-(1-methylethyl)- 1H-2,1,3-benzothiadiazine-2,2-dioxide A mixture of 4-(6-fluoroindol-3-yl)-1,2,5,6-tetrahydropyridine (8.68 g, 40.2 mmol, 1.05 equivalent), 1-(2-chloroethyl)-3,4-dihydro-3-(1-methylethyl)-1H-2,1,3-benzothiadiazine-2,2-dioxide (11.05 g, 38.3 mmol), anhydrous sodium carbonate (20.297 g, 0.192 mol, 5 equivalents) and de-ionised water (200 ml) was stirred (mechanical stirring) and warmed under reflux for 20 hours. After cooling to room temperature, the mixture was extracted with chloroform (3×150 ml). The bulked extracts were washed with water and then dried over magnesium sulfate. Filtration was followed by evaporation to dryness in vacuo to yield an orange solid (approximately 18 g). This material was purified further by chromatography on silica first using dichloromethane to remove some residual chloroethylated starting material and then eluting with ethyl acetate to remove final product. This yielded an orange solid which was triturated with a mixture of dichloromethane/diethyl ether. This gave a yellow solid after filtration, 3,4-dihydro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide, m.p. 80–82° C.

The free base was dissolved in methanol, phosphoric acid added and the precipitate filtered to yield the phosphate salt, m.p. 166–168° C.

Similarly prepared:

3,4-Dihydro-1-{2-[4-(6-fluoroindol-3-yl)-1,2,5,6-tetrahydro-1-pyridyl]-1-ethyl}-3-methyl-1H-2,1,3-benzothiadiazine-2,2-dioxide, m.p.175–177° C.

3,4-Dihydro-1-{2-[4-(6-fluoroindol-3-yl)-1,2,5,6-tetrahydro-1-pyridyl]-1-ethyl}-3-(methylpropyl)-1H-2,1,3-benzothiadiazine-2,2-dioxide, m.p.147–148° C.

3-n-Butyl-3,4-dihydro-1-{2-[4-(6-fluoroindol-3-yl)-1,2,5,6-tetrahydro-1-pyridyl]-1-ethyl}-1H-2,1,3-benzothiadiazine-2,2-dioxide. MS [M+H=483].

3,4-Dihydro-1-{2-[4-(6-fluoroindol-3-yl)-1,2,5,6-tetrahydro-1-pyridyl]-1-ethyl}-3-(2-methylprop-1-yl)-1H-2,1,3-benzothiadiazine-2,2-dioxide. MS [M+H=483].

3,4-Dihydro-3-(1,1-dimethylethyl)-1-{2-[4-(6-fluoroindol-3-yl)-1,2,5,6-tetrahydro-1-pyridyl]-1-ethyl}-1H-2,1,3-benzothiadiazine-2,2-dioxide, m.p. 145.8–146.4° C.

3,4-Dihydro-6-fluoro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide, m.p. 93–96° C.

Ethyl 3,4-Dihydro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide-6-carboxylate, m.p. 198–205.3° C.

3,4-Dihydro-1-{4-[4-(6-fluoroindol-3-yl)-1,2,5,6-tetrahydro-1-pyridyl]-1-butyl}-3-(1-methylethyl)-1H-2,1,3-benzothiadiazine-2,2-dioxide, m.p. 129.5–130.6° C.

3,4-Dihydro-1-{3-[4-(6-fluoroindol-3-yl)-1,2,5,6-tetrahydro-1-pyridyl]-1-propyl}-3-(1-methylethyl)-1H-2,1,3-benzothiadiazine-2,2-dioxide, m.p. 129.5–130.6° C.

3,4-Dihydro-1-{2-[4-(6-fluoroindol-3-yl)-1,2,5,6-tetrahydro-1-pyridyl]-1-ethyl}-3-ethyl-1H-2,1,3-benzothiadiazine-2,2-dioxide, m.p.142.6–143.3° C.

3,4-Dihydro-1-{2-[4-(6-fluoroindol-3-yl)-1,2,5,6-tetrahydro-1-pyridyl]-1-ethyl}-3-propyl-1H-2,1,3-benzothiadiazine-2,2-dioxide, m.p.208–210° C.

3,4-Dihydro-1-{2-[4-(6-fluoroindol-3-yl)-1-piperidinyl]-1-ethyl}-3-(1-methylethyl)-1H-2,1,3-benzothiadiazine-2,2-dioxide. MS [M+H]$^+$=471.

3,4-Dihydro-1-{2-[4-(7-fluoroindol-3-yl)-1-piperidinyl]-1-ethyl}-3-(1-methylethyl)-1H-2,1,3-benzothiadiazine-2,2-dioxide. MS [M+H]$^+$=471.

3,4-Dihydro-1-{2-[4-(7-fluoroindol-3-yl)-1,2,5,6-tetrahydro-1-pyridyl]-1-ethyl}-3-(1-methylethyl)-1H-2,1,3-benzothiadiazine-2,2-dioxide, MS [M+H]$^+$=469.

EXAMPLE 2

3,4-Dihydro-2,2-dioxo-1-{2-[4-(6-fluoroindol-3-yl)-1,2,5,6-tetrahydro-1-pyridyl]-1-ethyl}-3-(1-methylethyl)-1H-2,1,3-benzothiadiazine-6-carboxylic acid.

Prepared from ethyl 3,4-dihydro-2,2-dioxo-1-{2-[4-(6-fluoroindol-3-yl)-1,2,5,6-tetrahydro-1-pyridyl]-1-ethyl}-3-(1-methylethyl)-1H-2,1,3-benzothiadiazine-6-carboxylate by lithium hydroxide hydrolysis in aqueous tetrahydrofuran, m.p. 192.8–194.4° C.

EXAMPLE 3

6-Amino-3,4-dihydro-1-{2-[4-(6-fluoroindol-3-yl)-1,2,5,6-tetrahydro-1-pyridyl]-1-ethyl)-3-(1-(methylethyl)-1H-2,1,3-benzothiadiazine-2,2-dioxide.

1-(2-Chloroethyl)-3,4-dihydro-3-(1-methylethyl)-6-nitro-1H-2,1,3-benzothiadiazine-2,2-dioxide(1.67 g, 0.005 mol) prepared from 3,4-dihydro-3-(1-methylethyl)-6-nitro-1H-2,1,3-benzothiadiazine-2,2-dioxide (prepared from 4-nitroaniline and isopropyl sulfamoyl chloride by methods described above was dissolved in absolute ethanol (50 ml) and hydrogenated at 60 psi in the presence of 5% palladium on charcoal (0.2 g). After 1 hour and no further hydrogen uptake, the catalyst was filtered, washed with ethanol and the solution evaporated to dryness giving 6-amino-1-(2-chloroethyl)-3,4-dihydro-3-(1-methylethyl)-1H-2,1,3-benzothiadiazine-2,2-dioxide.

Potassium carbonate (0.75 g, 0.0052 mol) was dissolved in water (10 ml) and to this was added 6-amino-1-(2-chloroethyl)-3,4-dihydro-3-(1-methylethyl)-1H-2,1,3-benzothiadiazine- 2,2-dioxide (1.34 g, 0.0044 mol) and 4-(6-fluoroindol-3-yl)-1,2,5,6-tetrahydropyridine (1.03 g, 0.0048 mol). This suspension was heated with rapid stirring under nitrogen for 24 hours. After cooling, the product was extracted with chloroform (3×50 ml) and the fractions dried over magnesium sulfate. After filtering and removing the solvent, a solid was obtained (1.76 g) which was chromatographed on flash silica eluting with 5% methanol-dichloromethane. The product, 6-amino-3,4-dihydro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide was triturated with ether and dried in vacuo, m.p. 154.5–155.5° C.

3,4-Dihydro-1-{2-[4-(6-fluoroindol-3-yl)-1,2,5,6-tetrahydro-1-pyridyl]-1-ethyl)-6-methoxy-3-(1-methylethyl)-1H-2,1,3-benzothiadiazine-2,2-dioxide as a yellow amorphous solid, m.p. 142–145° C.

EXAMPLE 4

3,4-Dihydro-1-{2-[4-(6-fluoroindol-3-yl)-1,2,5,6-tetrahydro-1-pyridyl]-1-ethyl}-6-hydroxy-3-(1-methylethyl)-1H-2,1,3-benzothiadiazine-2,2-dioxide.

3,4-Dihydro-1-{2-[4-(6-fluoroindol-3-yl)-1,2,5,6-tetrahydro-1-pyridyl]-1-ethyl}-6-methoxy-3-(1-methylethyl)-1H-2,1,3-benzothiadiazine-2,2-dioxide(1.0 g, 2 mmol) was dissolved in dry dichloromethane (20 ml) and cooled to 0° C. Boron tribromide (2.2 ml, 1.0 M solution in dichloromethane) was added and stirred at ambient temperature for 16 hours. The solution was cooled to 0° C. and boron tribromide (3.2 ml) added. After pouring onto ice-water, the product was extracted with ethyl acetate (2×150 ml), extracts dried, filtered and the solvent removed to give a pale yellow solid (1.0 g) Column chromatography using flash silica eluting with 5% methanol/dichloromethane gave 3,4-dihydro-1-{2-[4-(6-fluoroindol-3-yl)-1,2,5,6-tetrahydro-1-pyridyl]-1-ethyl}-6-hydroxy-3-(1-methylethyl)-1H-2,1,3-benzothiadiazine-2,2-dioxide as a yellow solid, m.p. 80–82° C.

EXAMPLE 5

3,4-Dihydro-8-fluoro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide 1) A 3-necked round bottom flask equipped with a magnetic stirrer bar was charged with 2-fluoroaniline(2 g, 18 mmol) and Et$_3$N (3 ml, 21.6 mmol) in toluene (20 ml) and is treated at 0° C., under argon atmosphere, with isopropyl-sulfamoyl chloride (3.17 g, 19.8 mmol) and the temperature maintained below 15° C. After the addition, the reaction was allowed to warm to room temperature and maintained during 24 hours. Then the solvent was evaporated at vacuo and the residue was dissolved in EtOAc. The organic phase was washed with water, dried over Na$_2$SO$_4$, filtered and evaporated to dryness yielding 3.9 g of an oil, N-(2fluorophenyl-N'-(1-methylethyl) sulfamide, which was used without further purification. This oil and methanesulfonic acid (34 ml, 525 mmol) were dissolved in dry dichloromethane (80 ml) and the solution was treated at 0° C., under argon atmosphere, with a solution of trioxane (0.86 g, 9.6 mmol) in CH$_2$Cl$_2$ (20 ml). After 15 minutes, the mixture was poured onto a mixture ice-water. The aqueous phase was extracted three times with CH$_2$Cl$_2$. The organic phase is dried over Na$_2$SO$_4$, filtered and evaporated to dryness. The crude product was purified by flash chromatography using as eluent CH$_2$Cl$_2$/hexane (2:1) to give 3,4-dihydro-8-fluoro-3-(1-methylethyl)-1H-2,1,3-benzothiadiazine-2,2-dioxide.

2) A 3-necked round bottom flask equipped with a water condenser, thermometer and magnetic stirrer bar was charged with a mixture of 3,4-dihydro-8-fluoro-3-(1-methylethyl)-1H-benzothiadiazine-2,2-dioxide (1 g, 6.8 mmol) and NaH (400 mg, 17 mmol) was added at 0° C., under argon atmosphere, in DMF (20 ml). After 1 hour, there was added 1-bromo-2-chloroethane (1.4 ml, 17 mmol) and then the reaction was stirred at room temperature overnight. The reaction was quenched with a saturated solution of $NH_4Cl$ and poured into water. The aqueous phase was extracted with $CH_2Cl_2$, dried over $Na_2SO_4$ and evaporated to dryness yielding an oil, 1-(2-chloroethyl)-3,4-dihydro-8-fluoro-3-(1-methylethyl)-1H-2,1,3-benzothiadiazine-2,2-dioxide which was used without further purification.

Similarly prepared were:

1-(2-Chloroethyl)-3,4-dihydro-3-(1-methylethyl)-8-trifluoromethyl-1H-2,1,3-benzothiadiazine-2,2-dioxide from 2-trifluoromethylaniline and isopropylsulfamoyl chloride.

1-(2-Chloroethyl)-3,4-dihydro-8-methyl-3-(1-methylethyl)-1H-2,1,3-benzothiadiazine-2,2-dioxide from o-toluidine and isopropylsulfamoyl chloride.

8-Chloro-1-(2-chloroethyl)-3,4-dihydro-3-(1-methylethyl)-1H-2,1,3-benzothiadiazine-2,2-dioxide from 2-chloroaniline and isopropylsulfamoyl chloride.

EXAMPLE 6

3,4-Dihydro-8-fluoro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide A suspension of 1-(2-chloroethyl)-3,4-dihydro-8-fluoro-3-(1-methylethyl)-1H-2,1,3-benzothiadiazine-2,2-dioxide (1.35 g), 4-(6-fluoroindol-3-yl)-1,2,5,6-tetrahydropyridine (31.45 g, 6.7 mmol) and $Na_2CO_3$ (3.6 g, 34.6 mmol) in water (8 ml) was heated at 100° C. under argon atmosphere for 30 hours. After cooling to room temperature the product was extracted with dichloromethane. The organic phase was dried over $Na_2SO_4$ and evaporated to dryness. The crude mixture was purified by flash chromatography using as eluent $CH_2Cl_2$/MeOH (97:3) yielding 3,4-dihydro-8-fluoro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide as a pale brown solid.

1H-NMR (CDCl3, 200 Mz), d: 8.37 (broad s, 1H), 7.74 (dd,), 7.13–6.84 (m, 6H), 6.10 (broad s, 1H), 4.43 (s, 2H), 4.26 (m, 1H), 3.73 (t,2H), 3.25 (broad s, 2H), 2.97 (t, 2H), 2.76 (t, 2H), 2.49 (broad s, 2H), 1.25 (d,6H).

Similarly prepared were;

3,4-Dihydro-1-{2-[4-(6-fluoroindol-3-yl)-1,2,5,6-tetrahydro-1-pyridyl]-1-ethyl}-8-methyl-3-(1-methylethyl)-1H-2,1,3-benzothiadiazine-2,2-dioxide, m.p. 199–201° C.

3,4-Dihydro-8-chloro-1-(2-[4-(6-fluoroindol-3-yl)1,2,5,6-tetrahydro-1-pyridyl]-1-ethyl}-3-(1-methylethyl)-1H-2,1,3-benzothiadiazine- 2,2-dioxide hydrochloride MS [M+H]$^+$=503.1 (seen as free base),

EXAMPLE 7

Ethyl 3,4-dihydro-2,2-dioxo-1-{2-[4-(6-fluoroindol-3-yl)-1,2,5,6-tetrahydro-1-pyridyl]-1-ethyl}-1-3-(1-methylethyl)-1H-2,1,3-benzothiadiazine-8-carboxylate Ethyl 3,4-dihydro-2,2-dioxo-3-(1-methylethyl)-1-(prop-2-en-1-yl)-1H-2,1,3-benzothiadiazine-8-carboxylate (1.1 g)(prepared from ethyl 3,4-dihydro-2,2-dioxo-3-(1-methylethyl)-1H-2,1,3-benzothiadiazine-8-carboxylate and (prop-2-en-1-yl) bromide) was dissolved in dichloromethane (80 ml) and cooled to −75° C. Ozone was passed through the solution until the solution became blue. At which time, dimethyl sulfide (5 ml) was added and the solution allowed to come to room temperature over 1 hour. The solution was washed with water to remove the DMSO present, dried over anhydrous magnesium sulfate, filtered and evaporated in vacuo to give a solid, ethyl 3,4-dihydro-2,2-dioxo-3-(1-methylethyl)-1-(2-oxoethyl)-1H-2,1,3-benzothiadiazine-8-carboxylate. This was dissolved in dichloroethane (50 ml) containing glacial acetic acid(5 drops) together with 4-(6-fluoroindol-3-yl)-1,2,5,6-tetrahydropyridine (0.8 g, 1.1 equiv.). Sodium triacetoxy borohydride (0.8 g, 1.1 equiv.) was added and the solution stirred overnight at room temperature. After washing with 2N sodium hydroxide (30 ml) and brine, the solution was dried, filtered and evacuated in vacuo to yield an off-white solid. Column chromatography eluting with ethyl acetate/hexane to ethyl acetate gave the required product, ethyl 3,4-dihydro-2,2-dioxo-1-{2-[4-(6-fluoroindol-3-yl)-1,2,5,6-tetrahydro-1-pyridyl]-1-ethyl}-3-(1-methylethyl)-1H-2,1,3-benzothiadiazine-8-carboxylate, m.p. 95–97° C.

EXAMPLE 8

7-fluoro 3,4-dihydro-1-{2-[4-(6-fluoroindol-3-yl)-1,2,5,6-tetrahydro-1-pyridyl]-1-1-ethyl}-1-3-(1-methylethyl)-1H-2,1,3-benzothiadiazine-2,2-dioxide 1) To a solution of 4-fluoro-2-nitrotoluene (5 g, 32 mmol) in DMF (32 ml) was added dimethylformamide dimethyl acetal (5.56 ml, 42 mmol) and the mixture warmed at 140° C. for 18 hours in Argon atmosphere. Then the solution was allowed to reach room temperature and diethyl ether (100 ml) and water (100 ml) was added. The organic layer was washed with water (2×100 ml) and brine (1×100 ml), dried (MgSO$_4$) and solvent concentrated at reduced pressure, affording N,N-dimethyl-2-(4-fluoro-2-nitrophenyl) ethenylamine as a red solid. No further purification was necessary.

2) N,N-Dimethyl-2-(4-fluoro-2-nitrophenyl) ethenylamine (6.72 g, 32 mmol) and NaIO$_4$ (20.53 g, 96 mmol) were stirred in 50% aqueous THF (160 ml) at room temperature for 1.5 hours. The mixture was filtered in a celite pad and eluted with EtOAc. The organic layer was washed with NaHCO$_3$ (saturated solution, 3×100 ml), dried over Na$_2$SO$_4$ and concentrated in vacuo. The residue was purified by flash chromatography (50% CH$_2$Cl$_2$/hexane) affording 4-fluoro-2-nitro benzaldehyde as an orange oil.

3) To a solution of 4-fluoro-2-nitro benzaldehyde (3.76 g, 25 mmol) in dry MeOH (120 ml), was added isopropyl amine (2.1 ml, 25 mmol) and the mixture stirred for 2 hours at room temperature in Argon atmosphere. Then it was then transferred into a Parr bottle containing 5% Pd on charcoal (246 mg) under Argon and hydrogenated at 30 psi for 18 hours. The suspension was filtered over a celite pad, washed with MeOH and evaporated at reduced pressure to afford (2-amino-4-fluorophenyl)-N-(1-methylethyl)-methylamine as a yellow oil.

4) (2-Amino-4-fluorophenyl)-N-(1-methylethyl)-methylamine (1.47 g, 7.3 mmol) and sulfamide (703 mg, 7.3 mmol) were suspended in 8 ml of dry pyridine and the mixture stirred at 115° C. for 18 hours in Argon atmosphere. After cooling at room temperature the solvent was removed in vacuo and the residue dissolved in EtOAc (50 ml) and washed with 5N HCl (2×50 ml). Solvents were removed to afford 3,4-dihydro-7-fluoro-3-(1-methylethyl)-1H-2,1,3-benzothiadiazine-2,2-dioxide as a pale yellow solid.

5) A solution of 3,4-dihydro-7-fluoro-3-(1-methylethyl)-1H-2,1,3-benzothiadiazine-2,2-dioxide(1.48 g, 6.07 mmol) in dry DMF (15 ml) was added via a cannula to a flask containing sodium hydride (175 mg, 7.28 mmol) and DMF (2 ml) in Argon atmosphere, and stirred for 2 hours at room temperature when 1-bromo-2-chloroethane (7.28 mmol, 605

μl) was added dropwise. The mixture was stirred overnight at room temperature and water (75 ml) added. The product was extracted with EtOAc (3×50 ml) and the combined organic extracts were washed with water (1×100 ml) and then brine (1×100 ml), dried over sodium sulphate and solvent evaporated at reduced pressure. The residue was purified by flash chromatography on silica gel (EtOAc:Hexanes 1:4) affording pure 1-(2-chloroethyl)-3,4-dihydro-7-fluoro-3-(1-methylethyl)-1H-2,1,3-benzothiadiazine-2,2-dioxide.

6) To a 25 ml two-necked flask equipped with a reflux condenser and in Argon atmosphere, were added 1-(2-chloroethyl)-3,4-dihydro-7-fluoro-3-(1-methylethyl)-1H-2,1,3-benzothiadiazine-2,2-dioxide(678 mg, 2.2 mmol), 4-(6-fluoroindol-3-yl)-1,2,5,6-tetrahydropyridine (523 mg, 242 mmol), anhydrous $K_2CO_3$ (1.09 g, 11 mmol) and 10 ml of deionised water. The mixture was vigorously stirred under Argon for 64 hours at 100° C., allowed to reach room temperature and extracted with EtOAc (3×25 ml). The combined organic extracts were dried ($Na_2SO_4$) and solvent removed at reduced pressure. The residue was purified by flash chromatography on silica gel (EtOAc:hexane 1:3) affording 3,4-dihydro-1-{2-[4-(6-fluoroindol-3-yl)-1,2,5,6-tetrahydro-1-pyridyl]-1-ethyl}-3-(1-methylethyl)-7-fluoro-1H-2,1,3-benzothiadiazine-2,2-dioxide as a pale yellow solid, m.p. 103–105°.

$^1$H NMR (200 MHz, $CDCl_3$) δ 8.20 (br s, 1H), 7.79 (dd, 1H), 7.14 (d, 1H), 7.06 (t, 1H), 7.02 (d, 1H), 6.98 (s, 1H), 6.90 (dt, 1H), 6.78–6.65 (m, 2H), 6.16 (m, 2H), 4.58 (s, 2H), 4.19 (7x, 1H), 3.99 (dt, 2H), 3.33 (dd, 2H), 2.85 (dt, 2H), 2.62 (m, 2H), 1.12 (d, 6H).

Similarly prepared were:

3,4-Dihydro-1-{2-[4-(6-fluoroindol-3-yl)-1,2,5,6-tetrahydro-1-pyridyl]-1-ethyl}-3-(1-methylethyl)-7-trifluoromethyl-1H-2,1,3-benzothiadiazine-2,2-dioxide, m.p. 101–103° C.

1-{2-[4-(6-fluoroindol-3-yl)-1,2,5,6-tetrahydro-1-pyridyl]-1-ethyl}-7-methoxy-3-(1-methylethyl)-3,4-dihydro-1H-2,1,3-benzothiadiazine-2,2-dioxide, m.p. 88–900° C.

3,4-Dihydro-1-{2-[4-(6-fluoroindol-3-yl)-1,2,5,6-tetrahydro-1-pyridyl]-1-ethyl}-5-methyl-3-(1-methylethyl)-1H-2,1,3-benzothiadiazine-2,2-dioxide hydrochloride MS [M+H]=483.1 seen as free base 5-Chloro-3,4-dihydro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide hydrochloride MS [M+H]$^+$=503.1 seen as free base.

3,4-Dihydro-1-{2-[4-(6-fluoroindol-3-yl)-1,2,5,6-tetrahydro-1-pyridyl]-1-ethyl}-5-methoxy-3-(1-methylethyl)-1H-2,1,3-benzothiadiazine-2,2-dioxide, m.p. 72–74° C.

3,4-Dihydro-1-{2-[4-(6-fluoroindol-3-yl)-1,2,5,6-tetrahydro-1-pyridyl]-1-ethyl}-5-hydroxy-3-(1-methylethyl)-1H-2,1,3-benzothiadiazine-2,2-dioxide, m.p. 186–188° C.

3,4-Dihydro-5-fluoro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide, m.p. 107–109° C.

5-Bromo-3,4-dihydro-1-{2-[4-(6-fluoroindol-3-yl)-1,2,5,6-tetrahydro-1-pyridyl]-1-ethyl}-3-(1-methylethyl)-1H-2,1,3-benzothiadiazine-2,2-dioxide, m.p. 99–101° C.

EXAMPLE 9

1-{2-[4-(6-Fluoroindol-3-yl)-1,2,5,6-tetrahydro-1-pyridyl]-1-ethyl)-3-(1-methylethyl)-5-fluoro-3,4-dihydro-1H-2,1,3-benzothiadiazine-2,2-dioxide 1) To a solution of 4-fluoro-2-nitrotoluene (3 g, 17.96 mmol) in DMF (25 ml) was added $(MeO)_2CHNMe_2$ (3.12 ml, 23.35 mmol) and the mixture warmed at 140° C. for 4 hours in argon atmosphere. Then the solution was allowed to reach room temperature and diethyl ether (100 ml) and water (100 ml) was added. The organic layer was washed with water (2×100 ml) and brine (1×100 ml), dried ($MgSO_4$) and solvent concentrated at reduced pressure, affording an oil which was treated with $NaIO_4$ (11.5 g, 53.6 mmol). The mixture was stirred in 50% aqueous THF (100 ml) at room temperature for 24 hours. The mixture was filtered in a celite pad and eluted with EtOAc. The organic layer was washed with $NaHCO_3$(saturated solution, 3×100 ml), dried over $Na_2SO_4$ and concentrated in vacuo. The residue was purified by flash chromatography (50% $CH_2Cl_2$/Hexane) affording 2-nitro-6-fluorobenzaldehyde as a brown solid.

2) To a solution of 2-nitro-6-fluorobenzaldehyde(1.21 g, 7.16 mmol) in dry methanol (15 ml), was added isopropyl amine (1 ml, 11.4 mmol) and the mixture stirred for 24 hours at room temperature in argon atmosphere. Then $NaBH_4$ (0.3 g, 7.9 mmol) was added and the reaction mixture was stirred for 36 hours. The suspension was neutralized by addition of HCl 5N, then was extracted with diethyl ether (1×100 ml) and dried over $MgSO_4$ and evaporated at reduced pressure to afford N-(1-methylethyl)-(2-nitro-6-fluorophenyl) methylamine as a brown oil.

3) A suspension of N-(1-methylethyl)-(2-nitro-6-fluorophenyl)methylamine (0.4 g, 1.89 mmol), tin chloride dihydrate (1.75 g) in water (8 ml) was added HCl 12N (2 ml). The mixture was refluxed for 4 hours. Then, the reaction mixture was allowed to reach room temperature and was neutralized by addition of NaOH 2N and extracted with diethyl ether (1×100 ml), dried over $MgSO_4$ and evaporated under reduced pressure to afford N-(1-methylethyl)-(2-amino-6-fluorophenyl)methylamine.

4) N-(1-methylethyl)-(2-amino-6-fluorophenyl) methylamine (0.3 g, 1.6 mmol) and sulphamide (5.08 g, 2.5 mmol) were suspended in 7 ml of dry pyridine and the mixture stirred at 115° C. for 24 hours in argon atmosphere. After cooling at room temperature the solvent was removed in vacuo and the residue dissolved in EtOAc (50 ml) and washed with 5N HCl (2×50 ml). Solvents removal afforded 5-fluoro-3-(1-methylethyl)-3,4-dihydro-1H-2,1,3-benzothiadiazine-2,2-dioxide as a pale yellow solid.

5) A solution of 5-fluoro-3-(1-methylethyl)-3,4-dihydro-1H-2,1,3-benzothiadiazine-2,2-dioxide (0.22 g, 0.9 mmol) in dry DMF (15 ml) was added via cannula to a flask containing NaH (25 mg, 0.99 mmol) and DMF (7 ml) in argon atmosphere, and stirred for 2 hours at room temperature. 1-Bromo-2-chloroethane (0.19 ml, 2.25 mmol,) was then added dropwise and the mixture stirred at room temperature for 4 days. Then, the mixture was extracted with EtOAc (3×50 ml). The combined organic extracts were washed with water (1×100 ml) and then brine (1×100 ml), dried over $Na_2SO_4$ and solvent evaporated under reduced pressure. The residue was purified by flash chromatography on silica gel (EtOAc:Hexane 1:4) affording pure 1-(2-chloroethyl)-5-fluoro-3-(1-methylethyl)-3,4-dihydro-1H-2,1,3-benzothiadiazine- 2,2-dioxide.

1. To a 25 ml two-necked flask equipped with a reflux condenser and in argon atmosphere, were added 1-(2-chloroethyl)-5-fluoro-3-(1-methylethyl)-3,4-dihydro-1H-2,1,3-benzothiadiazine-2,2-dioxide(620 mg, 2.4 mmol), 6-fluoro-3-tetrahydropyridinylindole (0.79 g, 3.6 mmol), anhydrous $K_2CO_3$ (1.98 g, 12 mmol) and 10 ml of deionised water. The mixture was vigorously stirred under argon for 24 hours at 100° C., allowed to reach room temperature and extracted with EtOAc (3×25 ml). The combined organic extracts were dried (Na$_2$SO$_4$) and solvent removed at reduced pressure. The residue was purified by flash chromatography on silica gel (EtOAc:Hexane 1:3) affording 1-{2-[4-(6-fluoroindol-3-yl)-1,2,5,6-tetrahydro-1-pyridyl]-1-ethyl}-3-(1-methylethyl)-5-fluoro-3,4-dihydro-1H-2,1,3-benzothiadiazine-2,2-dioxide as a pale yellow solid, m.p. 107–109° C.

EXAMPLE 10

3,4-Dihydro-1-{2-[4-(6-fluoroindol-3-yl)-1,2,5,6-tetrahydro-1-pyridyl]-1-ethyl}-1-(1,3H)-2,1,3-benzothiadiazine-2,2-dioxide Anthranilonitrile was taken up in freshly distilled tetrahydrofuran and cooled to $-78°$ C. under nitrogen in a dry ice/acetone bath. Lithium diisopropyl amide (56.2 ml, 0.1142 mol, 2M solution in THF) was added and the mixture stirred for 10 minutes before (prop-2-en-1-yl) bromide (12.4 g, 0.1022 mol) was added dropwise. The mixture was stirred for a further 1 hour with cooling and then allowed to warm to room temperature, after which time aqueous ammonium chloride was added. The mixture was concentrated under reduced pressure, taken up in ethyl acetate, washed with aqueous ammonium chloride solution(3×100 ml), dried over anhydrous magnesium sulfate, filtered and concentrated under reduced pressure. The resulting oil was purified by chromatography on silica gel, eluent hexane/ethyl acetate (increasing % of ethyl acetate), to give N-(prop-2-en-1-yl) anthranilonitrile as a yellow oil.

Lithium aluminium hydride (5.0 g) was stirred in ether, under nitrogen at 0° C. N-(prop-2-en-1-yl) anthranilonitrile (13.2 g, 0.083 mol) was added dropwise and the mixture refluxed for 2 hours. Ethyl acetate was added and the mixture was washed with 2 molar NaOH(3×100 ml), the organics dried over anhydrous magnesium sulfate, filtered through celite and concentrated under reduced pressure to give an orange oil, N (prop-2-en-1-yl)-2-(ethanamine) aniline.

N-(prop-2-en-1-yl)-2-(ethanamine) aniline (14.2 g, 86 mmol) in pyridine (20 ml) was added dropwise to sulfamide (8.3 g) in pyridine (60 ml) at reflux. The reaction mixture was stirred at reflux under nitrogen for 2.5 hours, after which time 2N hydrochloric acid was added. The mixture was extracted with dichloromethane (3×100 ml),the organics collected and dried over anhydrous magnesium sulfate, filtered and concentrated under reduced pressure. Column chromatography on silica gel, (eluent ethyl acetate/hexane) gave 3,4-dihydro-1-(prop-2-en-1-yl)-(1,3H)-2,1,3-benzothiadiazine-2,2-dioxide as a solid.

To a 250 ml round bottomed flask containing dioxan(120 ml) and water(20 ml) was added 3,4-dihydro-1-(prop-2-en-1-yl)-1H-2,1,3-benzothiadiazine-2,2-dioxide (2.1 g, 9.1 mmol). A crystal of osmium tetroxide was added whereupon the solution turned black. Sodium periodate (3.54 g, 2.2 equivalents) in water (30 ml) was warmed to ensure dissolution and then added, causing the solution to turn a cloudy brown over 5 minutes. The reaction mixture was left overnight and filtered through celite. The product was extracted with ethyl acetate and the organics washed with water. The product was finally obtained as an oil by filtering through a flash silica pad eluting with 4:1 petrol ether/ethyl acetate.

To a dry 100 ml round bottomed flask containing powdered molecular sieves 4A (1.5 g) was added 3,4-dihydro-1-(2-oxoethyl)-1H-2,1,3-benzothiadiazine-2,2-dioxide (0.8 g, 3.54 mmol) in methanol (30 ml)and 4-(6-fluoroindol-3-yl)-1,2,5,6-tetrahydropyridine (0.76 g) dissolved in methanol (10 ml). Borane-pyridine (1 ml) was added after 1 hour and the solution stirred overnight. 5 MHCl (10 ml) was added followed by 50% sodium hydroxide solution(5 ml) and water(5 ml). Solution was filtered through celite and ethyl acetate(3×50 ml) added. The organics were collected, washed with water, dried, filtered and the solvent removed in vacuo. Column chromatography through flash silica eluting with ethyl acetate/hexane gave product, 3,4-dihydro-(1-(2-[4-(6-fluoroindol-3-yl)-1,2,5,6-tetrahydro-1-pyridyl]-1-ethyl}-1H-2,1,3-benzothiadiazine-2,2-dioxide, m.p. 183–185° C.

EXAMPLE 11

3,4-Dihydro-1-{2-[4-(6-fluoroindol-3-yl)-1,2,5,6-tetrahydro-1-pyridyl]-1-1-ethyl}-3,4,4-trimethyl-1H-2,1,3-benzothiadiazine-2,2-dioxide 2-Aminoacetophenone(5.6 g, 41.5 mmol)and sulfamide (4 g, 41.5 mm) were added to diglyme (70 ml, dried over 4A molecular sieves) and the solution heated under nitrogen at 150° C. After 1 hour a solid forms but heating was continued for 2 hours in total. After cooling, ether was added followed by 2N sodium hydroxide which dissolved the solid formed. The aqueous phase was collected, diluted with ethanol and (prop-2-en-1-yl) bromide (8 ml) added, stirring being continued overnight. After concentration under vacuo the residue was partitioned between water and ethyl acetate. The organic phase was collected, dried, over magnesium sulfate, filtered and the solvent evaporated under reduced pressure to yield a yellow oil, 3,4-dihydro-4-methyl-1-(prop-2-en-1-yl)-1H-2,1,3-benzothiadiazine-2,2-dioxide. 3,4-Dihydro-4-methyl-1-(prop-2-en-1-yl)-1H-2,1,3-benzothiadiazine-2,2-dioxide(2.4 g, 10 mmol) was dissolved in dry tetrahydrofuran (40 ml) under nitrogen and the solution cooled to −78° C. in an acetone/dry ice bath. Methyl magnesium bromide (5 ml, 3M solution in ether) was added at this temperature and kept for 30 minutes when it was allowed to come to room temperature. After stirring for 2 hours, water was added and the solution concentrated. Partitioning between ethyl acetate and dilute HCl(aq) and collection of the organic extracts followed by drying, filtering and removal of solvent gave a product showing 75% conversion to product. Column chromatography eluting with ethyl acetate/hexane gave product, 3,4-dihydro-4,4-dimethyl-1-(prop-2-en-1-yl)-1H-2,1,3-benzothiadiazine-2, 2-dioxide. This compound (1.85 g, 7.3 mmol) was dissolved in N-methylpyrrolidine (30 ml) under nitrogen and sodium hydride (350 mg) was added at room temperature resulting in a vigorous effervescence. After the gas evolution had subsided (30 minutes), methyl iodide (300 mg) was added and the solution stirred overnight. The reaction was poured onto water and extracted with ethyl acetate(3×50 ml). Organic phase was washed with water (2×100 ml), dried, filtered and vacced to an oil, 3,4-dihydro-1-(prop-2-en-1-yl)-3,4,4-trimethyl-1H-2,1,3-benzothiadiazine-2,2-dioxide.

3,4-Dihydro-1-(prop-2-en-1-yl)-3,4,4-trimethyl-1H-2,1,3-benzothiadiazine-2,2-dioxide (2.17 g) was taken up in dioxan (60 ml)/water (20 ml) and osmium tetroxide added (one crystal).

Reaction stirred at room temperature and sodium periodate (3.2 g) in water (25 ml) added. After stirring overnight, the reaction was filtered and concentrated. The residue dissolved in ethyl acetate/water, extracted, organics washed with water, dried, filtered and the solvent removed to yield an oil, 3,4-dihydro-1-(2-oxoethyl)-3,4,4-trimethyl-1H-2,1, 3-benzothiadiazine-2,2-dioxide.

Using conditions described above, reacting 4-(6-fluoroindol-3-yl)-1,2,5,6-tetrahydropyridine with 3,4-dihydro-1-(2-oxoethyl)-3,4,4-trimethyl-1H-2,1,3-benzothiadiazine-2,2-dioxide gave 3,4-dihydro-1-{2-[4-(6-fluoroindol-3-yl)-1,2,5,6-tetrahydro-1-pyridyl]-1-ethyl}-3,4,4-trimethyl-1H-2,1,3-benzothiadiazine-2,2-dioxide as a white solid, m.p. 193–6° C.

and similarly,
4-(6-Fluoroindol-3-yl)-1,2,5,6-tetrahydropyridine with 3,4-dihydro-4,4-dimethyl-1-(2-oxoethyl)-1H-2,1,3-benzothiadiazine-2,2-dioxide was obtained 3,4-dihydro-1-{2-[4-(6-fluoroindol-3-yl)-1,2,5,6-tetrahydro-1-pyridyl]-1-ethyl}-4,4-dimethyl-1H-2,1,3-benzothiadiazine-2,2-dioxide as a white solid, m.p. 158–160° C. as its hydrochloride salt.

EXAMPLE 12

3,4-Dihydro-1-{2-[4-(6-Fluoroindol-3-yl)-1,2,5,6-tetrahydro-1-pyridyl]-1-1-ethyl}-1-3,4-dimethyl-1H-2,1,3-benzothiadiazine-2,2-dioxide This compound was synthesised from 4-methyl-1-(prop-2-en-1-yl)-1H-2,1,3-benzothiadiazine-2,2-dioxide (prepared in the above example) as follows:

4-Methyl-1-(prop-2-en-1-yl)-1H-2,1,3-benzothiadiazine-2,2-dioxide(2 g) was dissolved in ethanol(50 ml) and treated with sodium borohydride (350 mg) at room temperature. After 15 minutes, the solvent was removed in vacuo and water added(200 ml). The product was extracted with chloroform(3×100 ml), dried, filtered and evaporated in vacuo to give a solid. This was dissolved in dry dimethylformamide (35 ml) and treated with sodium hydride (350 mg) at room temperature for 30 minutes followed by methyl iodide(600 µl). The reaction was stirred at room temperature for 1 hour, poured into water(250 ml), extracted with ether (3×75 ml), dried, filtered and the solvent removed to give 3,4-dihydro-3,4-dimethyl-1-(prop-2-en-1-yl)-1H-2,1,3-benzothiadiazine-2,2-dioxide. This product was dissolved in dioxan (25 ml) and treated with osmium tetroxide (2 crystals) and sodium periodate(3.6 g) in water(25 ml) and stirred at room temperature overnight. Water was added(100 ml) and the product extracted with ether(3×100 ml), dried, filtered and the solvent removed to give an oil. This was dissolved in methanol(50 ml) and treated with 4-(6-fluoroindol-3-yl)-1,2,5,6-tetrahydro-1-pyridine (1.2 g) at room temperature overnight in the presence of acetic acid(1 ml) and 3A molecular sieves(2 g). Sodium cyanoborohydride(1 g) was then added and the reaction stirred for 4 hours. A further quantity of acetic acid (1 ml) and sodium cyanoborohydride(1 g) were added and stirred at room temperature for 18 hours. Saturated sodium bicarbonate (250 ml) was added and the mixture extracted with ethyl acetate (3×100 ml). After drying, filtering and removal of solvent, flash chromatography on the residue eluting with chloroform/ethyl acetate to ethyl acetate gave product, 3,4-dihydro-1-{2-[4-(6-fluoroindol-3-yl)-1,2,5,6-tetrahydro-1-pyridyl]-1-ethyl}-3,4-dimethyl-1H-2,1,3-benzothiadiazine-2,2-dioxide, m.p.105–108° C.

EXAMPLE 13

3,4-Dihydro-1-{2-[4-(6-fluoroindol-3-yl)-1,2,5,6-tetrahydro-1-pyridyl]-1-ethyl}-4-(2-methylethyl)- -1H-2,1,3-benzothiadiazine-2,2-dioxide Sulfamoyl chloride was prepared in situ by cautiously adding to a solution of chlorosulfonyl isocyanate (7.05 g, 0.05 mol) in acetonitrile (50 ml) cooled to 0–5° C., water (0.9 ml) in acetonitrile (5 ml) keeping the temperature below 10° C., whilst stirring for 1 hour. A solution of 1-(prop-2-en-1-yl) aniline (6.65 g, 0.05 mol) and triethylamine (5.05 g, 0.05 mol) was stirred at 0–5° C. and the sulfamoyl chloride prepared above was added slowly keeping the temperature below 10° C., stirring overnight. The reaction was poured into ice-water(100 ml) and the product, 1-phenyl-1-(prop-2-en-1-yl) sulfamide was collected by filtration. This was treated with 2-methylpropionaldehyde and methane sulfonic acid as described previously to give 3,4-dihydro-4-(2-methylethyl)-1-(prop-2-en-1-yl)-1H-2,1,3-benzothiadiazine-2,2-dioxide. This compound was converted to 3,4-dihydro-4-(2-methylethyl)-1-(2-oxoethyl)-1H-2,1,3-benzothiadiazine-2,2-dioxide by methods discussed previously.

3,4-Dihydro-1-(2-[4-(6-fluoroindol-3-yl)-1,2,5,6-tetrahydro-1-pyridyl]-1-ethyl}-4-(2-methylethyl)-1H-2,1,3-benzothiadiazine-2,2-dioxide m.p. 196–198° C. was prepared from 4-(6-fluoroindol-3-yl)-1,2,5,6-tetrahydro-1-pyridine and 3,4-dihydro-4-(2-methylethyl)-1-(2-oxoethyl)-1H-2,1,3-benzothiadiazine-2,2-dioxide using previously described methods.

Similarly prepared was
3,4-Dihydro-1-{2-[4-(6-fluoroindol-3-yl)-1,2,5,6-tetrahydro-1-pyridyl]-1-ethyl}-4-spirocyclopentyl-1H-2,1,3-benzothiadiazine-2,2-dioxide m.p. 151–153° C. from 1-phenyl-1-(prop-2-en-1-yl) sulfamide and cyclopentanone as starting materials.
3,4-Dihydro-1-{2-[4-(6-fluoroindol-3-yl)-1,2,5,6-tetrahydro-1-pyridyl]-1-ethyl}-3-methyl-4-(2-methylethyl)-1H-2,1,3-benzothiadiazine-2,2-dioxide.

This compound can be prepared by previously mentioned methodology from 4-(6-fluoroindol-3-yl)-1,2,5,6-tetrahydro-1-pyridine and 3,4-dihydro-3-methyl-4-(2-methylethyl)-1-(2-oxoethyl)-1H-2,1,3-benzothiadiazine-2,2-dioxide (prepared from 3,4-dihydro-4-(2-methylethyl)-1-(prop-2-en-1-yl)-1H-2,1,3-benzothiadiazine-2,2-dioxide mentioned previously and methyl iodide, with sodium hydride as base) to give 3,4-dihydro-1-{2-[4-(6-fluoroindol-3-yl)-1,2,5,6-tetrahydro-1-pyridyl]-1-ethyl}-3-methyl-4-(2-methylethyl)-1H-2,1,3-benzothiadiazine-2,2-dioxide, m.p.180–182° C.

EXAMPLE 14

1{2-[4-(6-Fluoroindol-3-yl)-1,2,5,6-tetrahydro-1-pyridyl]-1-ethyl}-1-3,4,5,6,7,7a-hexahydro-1H-pyridor2,1-d1-2,1,3-benzothiadiazine-2,2-dioxide 2-(2'-Nitrophenyl)pyridine(3 g) was dissolved in acetic acid(30 ml) and hydrogenated at 70 psi over platinum oxide. After 1 hour, the product was filtered and the reaction concentrated, taken up in ethyl acetate (100 ml) and washed with 1N sodium hydroxide. After drying, filtering and removal of solvent a dark oil(2.5 g) was obtained. This was dissolved in pyridine(60 ml) with sulfamide (1.5 g, 15 mmol) and heated at reflux under nitrogen for 6 hours. After concentrating, it was partitioned between ether and 2N sodium hydroxide. To the aqueous phase was added an excess of 1-(prop-2-en-1-yl) bromide and DMF(20 ml)and the reaction warmed to 50° C. for 3 days. The reaction was concentrated and the residue taken up in ethyl acetate, washed with water(2×100 ml) and 2N hydrochloric acid(30 ml). The solvent was dried, filtered and evaporated to give, after suction filtration through flash silica eluting with hexane-ethyl acetate (1:4), an orange oil, 1-(prop-2-en-1-yl)-3,4,5,6,7,7a-hexahydro-1H-pyrido[2,1-d]-2,1,3-benzothiadiazine-2,2-dioxide. This was transformed with previously discussed methodology to give 1-{2-[4-(6-fluoroindol-3-yl)-1,2,5,6-tetrahydro-1-pyridyl]-1-ethyl}-3,4,5,6,7,7a-hexahydro-1H-pyrido[2,1-d]-2,1,3-benzothiadiazine-2,2-dioxide, m.p.135–137.7° C. as its hydrochloride salt.

EXAMPLE 15

3.4-Dihydro-1-{2-[3-(6-fluoroindol-3-yl)-pyrrolidinyl]-1-ethyl}-1-3-(1-methylethyl)-1H-2,1,3-benzothiadiazine-2,2-dioxide.

6-Fluoroindole(10.03 g, 74.29 mmol) and maleimide (21.62 g, 222.9 mmol) were added to a stirred solution of acetic acid under nitrogen and heated at reflux for 144 hours. The solution was then evaporated in vacuo, dissolved in ethyl acetate and washed with saturated sodium bicarbonate solution. The aqueous layer was re-extracted with ethyl acetate(2×150 ml) and the organics dried, filtered and evaporated in vacuo. Column chromatography eluting with petroleum ether and ether/petroleum ether gave the product as a yellow solid.

To a stirred solution of the 3-(6-fluoroindol-3-yl) pyrrolidinedione in dry tetrahydrofuran (150 ml) was added lithium aluminium hydride (8.58 g, 214.5 mmol) as a solid portionwise. After refluxing under nitrogen overnight, the reaction was cooled and hydrated sodium sulfate added. After the effervescence had subsided, water (1 ml) was added and the reaction filtered, the residue washed with methanol and then concentrated in vacuo to afford a brown solid, 3-{6-fluoro-indol-3-yl}-pyrrolidine. Column chromatography eluting with dichloromethane to dichloromethane:methanol:ammonia (9:1.5:0.1) gave an orange solid.

3-{6-Fluoro-indol-3-yl}-pyrrolidine (500 mg, 2.45 mmol), potassium carbonate (1.04 g, 9.8 mmol), and 1-(2-chloroethyl)-3,4-dihydro-3-(1-methylethyl)-1H-2,1,3-benzothiadiazine-2,2-dioxide (708 mg, 2.45 mmol) were refluxed in water (15 ml) under nitrogen overnight. The solid was dissolved in ethyl acetate(2×100 ml) and washed with brine, dried, filtered and evaporated in vacuo to afford a brown oil. Column chromatography eluting with ethyl acetate gave a yellow solid, 3,4-dihydro-1-{2-[3-(6-fluoroindol-3-yl)-pyrrolidinyl]-1-ethyl}-3-(1-methylethyl)-1H-2,1,3-benzothiadiazine-2,2-dioxide, m.p.50.8–54.4° C.

The following Examples illustrate typical formulations containing the compound of the invention.

EXAMPLE 16

Tablets each containing 10 mg of active ingredient are made up as follows:

| Active ingredient | 10 mg |
|---|---|
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 17

Capsules each containing 20 mg of medicament are made as follows:

| Active ingredient | 20 mg |
|---|---|
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

I claim:
1. A compound of the formula:

(I)

in which n is 1 or 2, m is 1 or 2, p is 1 to 6, q is 0 or 1 to 3, $R^1$ and $R^2$ are each hydrogen or $C_{1-4}$ alkyl, $R^3$, $R^4$ and $R^5$ are each hydrogen, $C_{1-4}$ alkyl, optionally substituted phenyl or optionally substituted phenyl-$C_{1-4}$ alkyl, or $R^3$ and $R^4$ together form an alkylene link of formula —$(CH_2)_3$— or —$(CH_2)_4$—, or $R^4$ and $R^5$ together with the carbon atom to which they are attached form a $C_{3-6}$ cycloalkyl group, $R^6$ is $C_{1-4}$ alkyl, $C_{1-4}$ alkoxy, carboxy, hydroxy, cyano, halo, trifluoromethyl, nitro or amino, the dotted line represents an optional double bond, and the fluorine atom is attached at the 6 or 7-position;

or a salt or ester thereof.

2. A compound according to claim 1 in which $R^3$ and $R^4$ are each hydrogen, $C_{1-4}$ alkyl, optionally substituted phenyl or optionally substituted phenyl-$C_{14}$ alkyl, and $R^5$ is hydrogen.

3. A compound according to either of claims 1 or 2, in which the fluorine substituent is at the 6-position, and in which the dotted line represents a double bond.

4. A compound according to claim 3 in which n is 2 and m is 1, $R^1$ and $R^2$ are both hydrogen and p is 2.

5. A compound according to claim 1 of the formula:

in which $R^3$ is $C_{1-4}$ alkyl, or a pharmaceutically acceptable salt thereof.

6. A pharmaceutical formulation comprising a compound according to claim 1, or a pharmaceutically acceptable salt or ester thereof, together with a diluent or carrier therefor.

7. A method of treating a disorder of the central nervous system which comprises administering an effective amount of a compound according to claim 1, or a pharmaceutically acceptable salt or ester thereof.

8. A compound according to claim 4 wherein $R^3$ is $C_{1-4}$ alkyl, $R^4$ and $R^5$ are hydrogen and q is 0.

* * * * *